United States Patent [19]

Kaeding

[11] 4,117,024

[45] Sep. 26, 1978

[54] ETHYLATION OF AROMATIC COMPOUNDS

[75] Inventor: Warren W. Kaeding, Westfield, N.J.

[73] Assignee: Mobil Oil Corporation, New York, N.Y.

[21] Appl. No.: 820,051

[22] Filed: Jul. 29, 1977

[51] Int. Cl.$^2$ ................................................ C07C 3/52
[52] U.S. Cl. .............................. 260/671 R; 260/671 C
[58] Field of Search ........................ 260/671 R, 671 C

[56] References Cited

U.S. PATENT DOCUMENTS

| 3,716,597 | 2/1973 | Mitsche et al. | 260/671 C |
| 3,962,364 | 6/1976 | Young | 260/671 C |
| 4,016,218 | 4/1977 | Haag et al. | 260/671 C |

Primary Examiner—Delbert E. Gantz
Assistant Examiner—C. E. Spresser
Attorney, Agent, or Firm—Charles A. Huggett; Raymond W. Barclay

[57] ABSTRACT

A catalytic process is provided for the ethylation of mono alkyl benzenes wherein the alkyl substituent contains 1 or 2 carbon atoms, i.e., toluene or ethylbenzene, by contacting the same with ethylene in the presence of hydrogen under conversion conditions including a temperature between about 350° and about 500° C, a pressure greater than atmospheric but less than 400 psig, employing a hydrogen to ethylene mole ratio in the approximate range of 0.5 to 10 and in the presence of a catalyst comprising a crystalline aluminosilicate zeolite, which zeolite is characterized by an activity in terms of alpha value, of between about 2 and about 5000, a xylene sorption capacity greater than 1 gram/100 grams of zeolite and an ortho zylene sorption time for 30% of said capacity of greater than 10 minutes, said sorption capacity and sorption time being measured at 120° C and a xylene pressure of 4.5 ± 0.8 mm. of mercury, said crystalline aluminosilicate zeolite further being characterized by a silica to alumina of at least about 12 and a constraint index, as hereinafter defined, within the approximate range of 1 to 12, whereby aging of said catalyst during ethylation is substantially reduced over comparable reaction carried out in the absence of hydrogen.

14 Claims, No Drawings

ETHYLATION OF AROMATIC COMPOUNDS

BACKGROUND OF THE INVENTION

1. Field of the Invention

This invention relates to a process for ethylation of toluene or ethylbenzene utilizing a specified crystalline aluminosilicate zeolite catalyst in the presence of hydrogen under conditions such that aging of the catalyst is retarded.

2. Description of the Prior Art

Alkylation of aromatic hydrocarbons utilizing crystalline aluminosilicate catalysts has heretofore been described. U.S. Pat. No. 2,904,697 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

While the above-noted prior art is considered of interest in connection with the subject matter of the present invention, the ethylation process described herein carried out in the presence of hydrogen under specified conditions utilizing catalyst of aluminosilicate zeolite, said zeolite having a silica/alumina ratio of at least about 12 and a constraint index of 1 to 12, which catalyst has undergone prior modifications to alter the activity and sorption characteristics thereof has not, insofar is known, been heretofore described.

Ethyltoluene and diethylbenzene are valuable chemicals. Ethyltoluene may be dehydrogenated to produce vinyltoluene. The latter is used, to a large extent, in fiber-reinforced polyesters where the low volatility of vinyltoluene and the reduced shrinkage in the final product make it superior over corresponding use of styrene. The vinyltoluene is also used to a large extent in alkyd paints where it has the advantage over styrene of higher flash points and better film toughness. Copolymers of vinyltoluene with butadiene and with alpha-methylstyrene are used in adhesives, traffic paints, inks and hot melts, where the principal advantages are rapid dry or cure time.

It has heretofore been recognized that the presence of substantial quantities of the ortho isomers is highly undesirable in the charge undergoing dehydrogenation since it tends to lead to ring closure with formation of the corresponding indenes and indanes which adversely affect the properties of the resultant polymer. The indenes and indanes so formed are difficult to separate from the desired vinyl aromatic products. It has accordingly heretofore been necessary to remove the ortho isomers from the ethyltoluene and diethylbenzene charge stocks by expensive distillation techniques prior to dehydrogenation thereof.

It is evident that the availability of ethyltoluene or diethylbenzene in which the ortho isomer is initially absent or present only in trace amount would eliminate the necessity for expensive prior removal of this isomer. Such products have, however, not heretofore been available.

A prevalent problem in effecting ethylation of toluene or ethylbenzene in the presence of the specified crystalline aluminosilicate catalyst has been undesired aging of the catalyst during ethylation, requiring frequent regeneration thereof in order to maintain the necessary activity. In alkylating reactions carried out with an olefinic reagent in the presence of hydrogen, an undesired reduction occurs to produce the corresponding paraffin. With ethylene, for example, substantial quantities of ethane are formed under many conditions and with many catalysts. As will be evident, this respresents a loss and downgrading of an expensive reagent.

SUMMARY OF THE INVENTION

In accordance with the present invention, a process has been discovered for ethylating toluene or ethylbenzene under particularly defined conditions in the presence of hydrogen and a specified crystalline aluminosilicate catalyst. It has been established that under the specified conditions in the presence of hydrogen and with the crystalline aluminosilicate catalyst employed, little, if any ethylene, was hydrogenated to form ethane. It has further been found that effecting the desired ethylation reaction in the presence of hydrogen serves to substantially reduce aging of the catalyst over a comparable reaction carried out in the absence of hydrogen.

In further embodiment, a process is provided for producing ethyltoluene or diethylbenzene virtually free of the undesired ortho isomer thereof eliminating the heretofore necessary expensive purification procedure. Following the teachings of this invention, para-ethyltoluene or para-diethylbenzene may be selectively produced herein as the sole isomer or as the major isomer in admixture with a minor amount of the meta- isomer together with trace amount or none of the ortho isomer. The process of the invention involves ethylation of toluene or ethylbenzene by contacting the same with ethylene under specified conditions of temperature, pressure and hydrogen concentration in the presence of a catalyst having a controlled hexane cracking activity, a minimum diffusion time for orthoxylene and a minimum xylene sorption capacity. More particularly, the zeolite utilized herein is characterized by an activity in terms of alpha value of between about 2 and about 5000, a xylene sorption capacity greater than 1 gram/100 grams of zeolite and an ortho xylene sorption time for 30% of said capacity of greater than 10 minutes, where the sorption capacity and sorption time are measured at 120° C. and a xylene pressure of 4.5 ± 0.8 mm. of mercury.

In a preferred embodiment, the present process comprises ethylation of toluene or ethylbenzene to yield ethyltoluene or diethylbenzene in which the proportion of the para isomer is substantially in excess of the normal equilibrium concentration and preferably in excess of 50 weight percent of the total ethyltoluene or diethylbenzene product in the presence of the specified catalyst.

Ethylation is effectively accomplished at a temperature between about 350° and about 500° C. at a pressure greater than atmospheric but less than 400 psig and preferably between about 50 and about 350 psig, in the presence of hydrogen, employing a hydrogen to ethylene mole ratio in the approximate range of 0.5 to 10 and preferably in the approximate range of 1 to 5 utilizing a feed weight hourly space velocity (WHSV) between about 3 and about 100. It will be understood that the pressure specified refers to the total pressure of mono alkyl benzene, ethylene and hydrogen. The specified WHSV is based upon the weight of catalyst composition, i.e., total weight of active catalyst and binder therefor. The molar feed ratio of mono alkyl benzene/ethylene is generally between about 1 and about 10.

DESCRIPTION OF SPECIFIC EMBODIMENTS

The aromatic compound undergoing ethylation in accordance with this invention is a mono alkyl-substituted benzene in which the alkyl substituent is methyl or ethyl, i.e., toluene or ethylbenzene. The ethylating agent employed is ethylene or a gaseous mixture high in this reactant.

In accordance with the present invention, the above described reactants, together with hydrogen, are brought into contact under critical conversion conditions with a specified crystalline aluminosilicate catalyst. The reaction conditions employed include a temperature between about 350° and about 550° C. and pressure greater than atmospheric but less than 400 psig and preferably between about 50 and about 350 psig and still more particularly between about 100 and 300 psig. It has been found that the substantial reduction in catalyst aging realized with the process of the present invention is not achieved at atmospheric pressure. On the other hand, at a pressure of about 400 psig or more undesired hydrogenation, of the ethylene reactant to ethane is encountered to a substantial degree. Accordingly, it is essential that the ethylation process described herein take place in the presence of hydrogen under pressure conditions greater than atmospheric but less than 400 psig.

The crystalline aluminosilicate catalyst employed herein is characterized by: (1) an activity in terms of alpha value of between about 2 and about 5000, (2) a xylene sorption capacity greater than 1 gram/100 grams of zeolite, and (3) an ortho xylene sorption time of 30% of said capacity of greater than 10 minutes, where the sorption capacity and sorption time are measured at 120° C. and xylene of 4.5 ± 0.8 mm. of mercury.

The alpha value reflects the relative activity of the catalyst with respect to a high activity silica-alumina cracking catalyst. To determine the alpha value, as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e., the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278–287, 1966.

The measurements of hydrocarbon sorption capacities and rates are conveniently carried out gravimetrically in a thermal balance. In particular, it has been found that an equilibrium sorption capacity in xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5 ± 0.8 mm. of mercury and an ortho-xylene sorption time for 30 percent of said capacity of greater than 10 minutes (at the same conditions of temperature and pressure) are required in order to achieve the desired selective production of para and meta diethyltoluenes.

It has been found that zeolites exhibiting the desired selectivity require a very long time up to and exceeding a thousand minutes to sorbo-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

$t_{0.3} = F \cdot t_{0.05}$

| Percent of sorption capacity | Factor(F) to Estimate 30% Sorption Time |
|---|---|
| 5 | 36 |
| 10 | 9 |
| 20 | 2.2 |

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |

-continued

| CAS | C.I. |
| --- | --- |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein with the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38, and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNameeGeorgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The crystalline aluminosilicate zeolites employed may be modified prior to use by combining therewith a small amount, generally in the range of about 0.5 to about 40 weight percent, preferably of a difficulty reducible oxide, such as the oxides of phosphorus, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phsophonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, monoammonium diacidphosphate, diammonium mono-acid phosphate, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.5 percent by weight. However, it is preferred that the amount of phosphorus in the zeolite be at least about 2 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium proprionate, magnesium 2-ethylhexoate, magnesium carbonate, magnesium, formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, i.e. up to about 500° C. are preferred. Heating is generally carried out for 1–5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 1 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron-containing compound is, for example, trimethylborate, a hydrocarbon solvent such as n-octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite such as nitrogen or helium or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, i.e. up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of boron incorporated with the zeolite should be at least about 0.2 percent by weight. However, it is preferred that the amount of boron in the zeolite be at least about 1 percent by weight when the same is combined with a binder, e.g. 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally, the amount of $Sb_2O_3$ in the composite catalyst will be between about 6 and about 40 weight percent and preferably between about 10 and about 35 weight percent. Antimony derivatives which may be used include: the hydrides $SbH_3$; the halides $MX_3$, $MX_5$ (M = Sb, X = F, Cl, Br, I); organic alkyl and aryl stibines and their oxides $R_3Sb$, $R_5Sb$, $R_xSb=O$ (R-alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)6$; organic acids such as $RSbO(OH)_2$, $R_2SbO \cdot OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; and antimonyl salts as $(SbO)SO_4$, $(SbO)NO_3$, $K(SbO)C_4H_4O_6$, $NaSbO_2 \cdot 3H_2O$.

In some instances, it may be desirable to modify the crystalline aluminosilicate zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 0.5 and about 40 weight percent.

It is also feasible to dilute or physically mix particles of the above-described crystalline aluminosilicate zeolites with particles of material substantially devoid of catalytic activity, such as, for example, low surface are quartz or with particles having appropriate catalytic activity and which may be either amorphous or crystalline.

The crystalline aluminosilicate zeolite catalyst employed may be treated prior to use with an atmosphere containing from about 5 to about 100 percent steam at a temperature of from about 250° to about 1000° C. for a period of between about 0.5 and about 100 hours and preferably at a temperature between about 400° C. and about 700° C. for a period of between about 1 and about 24 hours and under pressures ranging from sub-atmospheric to several hundred atmospheres to reduce the alpha value thereof, where the initial alpha value was greater than 500, to less than 500 preferably less than 20 but greater than zero.

It is also within the purview of this invention that the hereindescribed zeolite catalyst may, in some instances, desirably undergo precoking prior to the specified steam treatment. Precoking can be accomplished by contacting the catalyst with a hydrocarbon charge, e.g. toluene, under high severity conditions for a sufficient time to deposit the desired amount of coke thereon. Generally, between about 2 and about 75 and preferably between about 15 and about 75 weight percent of coke is deposited on the catalyst when the precoking technique is employed.

It has further been found that the crystal size of the crystalline aluminosilicate zeolite employed is a factor influencing the desired selective production of para ethyltoluene or diethylbenzene with suppression of the formation of the ortho isomer. While microcrystalline zeolites of the type described hereinabove having a crystal size in the approximate range of 0.01 to 0.10 micron may be employed, it is a preferred embodiment of the invention to utilize crystalline aluminosilicate zeolites of a crystal size greater than about 1 micron and generally in the approximate range of 1 to 40 microns. Particularly preferred are those zeolites having crystal sizes within the approximate range of 1 to 6 microns since it has been established that the use of such size crystals, steam treated, as described hereinabove, the production of the undesired ortho isomer is eliminated.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500°-550° C.

The following examples will serve to illustrate the process of this invention without limiting the same:

EXAMPLE 1

A sample of HZSM-5 having a crystallite size of approximately 2 microns, containing 35 percent alumina binder, in the form of 1/16' extrudate was treated with steam at a temperature of 600° C. for a period of 1 hour. The steamed material was then soaked in a 25.4 weight percent aqueous solution of diammonium acid phosphate, filtered, dried and calcined at 500° C. to give a phosphorus content of 3.35 weight percent. The catalyst was then cooled and treated in a similar manner with a 60 weight percent aqueous solution of magnesium acetate tetrahydrate, filtered, dried and calcined at 500° C. in air to provide a catalyst composition which contained 4.01 weight percent of magnesium and 3.11 weight percent of phosphorus.

EXAMPLE 2

Alkylation of toluene with ethylene to produce ethyltoluene was carried out in the presence of the catalyst of Example 1. A temperature of 400° C. was used and a pressure of 100 psig. Two runs were made, one in the absence of hydrogen utilizing a weight hourly space velocity to toluene/ethylene of 30/1.1 and the second in the presence of hydrogen. In the latter case, a weight hourly space velocity of toluene/ethylene/hydrogen of 30/1.1/0.08 was employed utilizing equimolar amounts of hydrogen and ethylene. In each instance, the resultant effluent streams were cooled and the liquid and gaseous products were weighed, measured and analyzed. The results for the two runs are summarized below in Table I.

As will be seen, in the first run only toluene and ethylene were fed to the catalytic reactor. In a period of 20 hours, toluene conversion decreased from 11.0 to 4.8 percent. Although substantial amounts of the desired para- and meta-ethyltoluene were produced, the aging rate was relatively high. It was necessary to regenerate the catalyst by calcination with air diluted with nitrogen to restore a satisfactory high toluene conversion rate.

The next series of runs show the results of cofeeding equimolar amounts of hydrogen and ethylene. In this case, the amount of desired ethyltoluene produced was similar to that obtained above. However, the catalyst aging rate was substantially reduced. Thus, in the first 21 hour period, the toluene conversion went from 10.7 to 8.9 percent. After a total of 120 hours of operation, toluene conversion went from 10.7 to 5.3 percent, a level of aging less than that observed for a period of only 20 hours in the process run where hydrogen was not used. It is evident that the aging rate was substantially reduced by cofeeding hydrogen and that the frequency required for catalyst regeneration can accordingly be significantly reduced.

EXAMPLE 3

In a manner similar to that described in Example 2, and with the identical catalyst, freshly calcined in air, a mixture of toluene, ethylene and hydrogen, at a weight hourly space velocity of 27.8/2.7/0.19 respectively, utilizing a molar ratio of 3.1/1.0/1.3 was fed to the reactor at a pressure of 400 psig and a temperature of 425° C. An exothermic reaction occurred which required a substantial reduction in heat input to the reactor furnace to maintain the desired temperature. The reaction product was primarily gaseous. The toluene and ethylene conversions were relatively low, 4 and 32% respectively, and the selectivity to products was primarily to ethane, 76%, other light gases 11% and ethyltoluenes were only 13% of the total.

It can be seen that at this relatively high pressure, that the major reaction observed was the undesired reduction of ethylene to ethane, a highly exothermic reaction.

EXAMPLE 4

In another series of runs, with the identical catalyst described in Example 1, the effect of feeding several diluents on catalyst aging was tested. Approximately equimolar amounts of nitrogen, hydrogen and toluene were used as "diluents" for an approximately 7.5/1 molar toluene/ethylene feed. The conditions of reactions and results are summarized below in Table II.

TABLE I

| Molar Ratio $H_2/C_2H_4$ | Time Hours | Conversion, % Tol | Conversion, % $C_2H_4$ | % Select to $C_2H_6$ | % Para in ET | Selectively to Products, % p-ET | m-ET | o-ET | Light Gas | Other Aromatics |
|---|---|---|---|---|---|---|---|---|---|---|
| 0/1 | (a) 0–20 | (b) 11.0–4.8 | 86–35 | .4–.3 | 95.6–97.3 | 86.5–97.7 | 4.0–2.6 | 0 | 1.8–1.3 | 2.7–1.5 |
| 1/1 | (a) 0/21 | 10.7–8.9 | 81–63 | .3 | 96.0–96.7 | 88.7–93.0 | 3.7–3.2 | 0 | 1.6–1.2 | 6.0–2.6 |
| 1/1 | 21–46 | 8.9–8.0 | 63–55 | .3–.2 | 96.7–97.2 | 93.0–94.1 | 3.2–2.8 | 0 | 1.2–1.1 | 2.6–2.1 |
| 1/1 | 46/76 | 8.0–6.9 | 55–44 | .2–.3 | 97.2–97.4 | 94.1–94.6 | 2.8–2.6 | 0 | 1.1–1.7 | 2.1–1.1 |
| 1/1 | 76–120 | 6.9–5.3 | 44–41 | .3 | 97.4–97.8 | 94.6–95.7 | 2.6–2.1 | 0 | 1.7 | 1.1–.5 |

(a)Catalyst calcined in air
(b)Range shows analysis for first and last hour of time period run.
(c)ET = Ethyltoluene

TABLE II

| Run No. | Temp. °C | Hrs. Run | Pressure psig | WHSV Toluene/$C_2H_4$/Other | Total | Mole Ratio Toluene/$C_2H_4$/Other | Aging Rate % Conv Hr[a] | Aging Rate ½ Conv. Hr.[b] | Initial Conv. Theoretical Maximum | % para-ethyltoluene total ethyltoluene |
|---|---|---|---|---|---|---|---|---|---|---|
| 1 | 425 | 20 | 200 | 38.2/1.5/0 | 39.7 | 7.6/1/0 | .465 | 13 | 12.4 / 13.15 | 95.1–96.6 |
| 2 | 425 | 20 | 200 | Toluene 27.9/1.1/11.2 | 40.2 | 7.5/1/3 | .0550 | 87 | 9.6 / 9.5 | 94.3–96.4 |
| 3 | 425 | 20 | 200 | $N_2$ 27.9/1.1/3.3 | 32.3 | 7.5/1/3 | .080 | 79 | 12.7 / 13.3 | 93.8–96.2 |
| 4 | 425 | 19 | 200 | $H_2$ 27.9/1.1/.24 | 29.2 | 7.5/1/3 | 0 | ∞ | 11.6 / 13.3 | 93.0–94.7 |

[a]Average reduction in % toluene conversion per hour over the time period tested
[b]Calculated time in days, based on the rate shown in (a) for the initial toluene conversion to be reduced by 50%

It will be evident that all of the diluents reduce the aging rate, including the toluene feed itself. However, with hydrogen, no aging at all was detected over the time period tested.

EXAMPLE 5

In another series of runs, with the identical catalyst described in Example 1 and in a manner similar to Example 2, the effect of diluting the toluene and ethylene feed to the reactor with nitrogen and hydrogen on catalyst aging was respectively tested and compared. The conditions in each instance included a temperature of 425° F., a pressure of 100 psig and a mole ratio of toluene/ethylene/diluent gas of 8/1/3. This corresponds in the case of nitrogen to a toluene/ethylene/nitrogen WHSV of 30/1.1/3.6 and in the case of hydrogen to a toluene/ethylene/hydrogen WHSV of 30/1.1/0.24. The products of reaction are summaried below in Tables III and IV, respectively.

It will be evident from Table III that when nitrogen was used the toluene and ethylene conversions were reduced from 10.7 to 6.3% and 86.6 to 48.4% respectively, over a 47 hour period. On the other hand, it will be seen from Table IV that when an equimolar amount of hydrogen was substituted for nitrogen, the catalyst aging rate was reduced significantly. Thus, toluene conversion was reduced from 10.5 to 10.0% and ethylene conversion from 92.1 to 87.9% in a 48 hour period. The distribution of ethyltoluene isomers and side reaction products was substantially the same in each instance. It will thus be seen that by cofeeding hydrogen, the frequency required to calcination with air to regenerate the catalyst can be significantly reduced.

EXAMPLE 6

In a manner similar to that described in Example 5 using a temperature of 425° C., a pressure of 100 psig and a feed of toluene/ethylene/hydrogen in a mole ratio

TABLE III

| Run No. | Stream Time Hrs. | Mole % Conv. Toluene | Mole % Conv. $C_2H_4$ | Selectivity to Products, wt. % Ethyltoluene | Selectivity to Products, wt. % Other Aromatics | Selectivity to Products, wt. % Light Gas | Isomers in Ethyltoluene in Products, % Para | Isomers in Ethyltoluene in Products, % Meta | Isomers in Ethyltoluene in Products, % Ortho |
|---|---|---|---|---|---|---|---|---|---|
| 1 | 1 | 10.7[a] | 86.6 | 91.7 | 6.5 | 1.8 | 95.3 | 4.7 | 0 |
| 2 | 1 | 10.5 | 83.9 | 94.1 | 4.5 | 1.4 | 95.5 | 4.5 | 0 |
| 3 | 1 | 10.2 | 81.3 | 95.1 | 3.8 | 1.2 | 95.6 | 4.4 | 0 |
| 4 | 1 | 10.0 | 79.7 | 96.0 | 2.9 | 1.1 | 85.7 | 4.3 | 0 |
| 5 | 20[b] | 9.1 | 71.0 | 97.3 | 1.8 | .9 | 96.2 | 3.8 | 0 |
| 6 | 1 | 7.8 | 62.6 | 97.9 | 1.5 | .6 | 96.3 | 3.7 | 0 |
| 7 | 1 | 7.8 | 60.7 | 98.0 | 1.4 | .6 | 96.3 | 3.7 | 0 |
| 8 | 19[b] | 7.2 | 54.3 | 98.0 | 1.3 | .7 | 96.6 | 3.4 | 0 |
| 9 | 1 | 6.4 | 48.7 | 98.1 | 1.2 | .7 | 96.7 | 3.3 | 0 |
| 10 | 1 | 6.3 | 48.4 | 98.2 | 1.1 | .7 | 96.7 | 3.3 | 0 |

[a]Maximum theoretical conversion is 12.4% based on limited amount of ethylene in the feed.
[b]Analysis based on entire product produced for time period indicated.

TABLE IV

| Run No. | Stream Time Hrs. | Mole % Conv. Toluene | Mole % Conv. $C_2H_4$ | Selectivity to Products, wt. % Ethyltoluene | Selectivity to Products, wt. % Other Aromatics | Selectivity to Products, wt. % Light Gas | Isomers in Ethyltoluene in Products, % Para | Isomers in Ethyltoluene in Products, % Meta | Isomers in Ethyltoluene in Products, % Ortho |
|---|---|---|---|---|---|---|---|---|---|
| 1 | 1 | 10.5[a] | 92.1 | 89.4 | 8.0 | 2.6 | 95.0 | 5.0 | 0 |
| 2 | 1 | 10.6 | 91.4 | 91.6 | 6.7 | 1.7 | 95.1 | 4.9 | 0 |
| 3 | 3[b] | 10.6 | 90.4 | 93.2 | 5.6 | 1.2 | 95.2 | 4.8 | 0 |
| 4 | 1 | 10.6 | 90.0 | 93.8 | 5.1 | 1.1 | 95.2 | 4.8 | 0 |
| 5 | 17[b] | 10.5 | 88.6 | 94.8 | 4.2 | 1.0 | 95.4 | 4.6 | 0 |
| 6 | 1 | 10.1 | 88.2 | 96.0 | 3.2 | .8 | 95.6 | 4.4 | 0 |
| 7 | 5 | 10.1 | 88.4 | 95.6 | 3.7 | .7 | 95.6 | 4.4 | 0 |
| 8 | 1 | 10.1 | 87.8 | 95.6 | 3.6 | .8 | 95.7 | 4.4 | 0 |
| 9 | 17[b] | 10.2 | 87.6 | 95.7 | 3.5 | .8 | 95.8 | 4.2 | 0 |
| 10 | 1 | 10.0 | 87.9 | 95.8 | 3.4 | .8 | 95.8 | 4.2 | 0 |

[a]Maximum theoretical conversions is 12.4% based on limited amount of ethylene in the feed.
[b]Analysis based on entire product produced for time period indicated.

respectively of 8/1/3 corresponding to a toluene/ethylene/hydrogen WHSV of 30/1.1/0.24, a run of approximately 9 days duration was made. The products of reaction are summarized below in Table V.

30.2/1.2/0.24 and with nitrogen, the ethylbenzene/ethylene/nitrogen WHSV was 30.2/1.2/3.36.

The gaseous feed mixture was passed over the catalyst and the condensed liquid and gaseous products

TABLE V

| Day No. | Stream Time Hrs. | Mole % Conv. Toluene | Mole % Conv. C$_2$H$_4$ | Selectivity to Products, wt. % Etyltoluene | Selectivity to Products, wt. % Other Aromatics | Selectivity to Products, wt. % Light Gas | Isomers in Ethyltoluene in Products, % Para | Isomers in Ethyltoluene in Products, % Meta | Isomers in Ethyltoluene in Products, % Ortho |
|---|---|---|---|---|---|---|---|---|---|
|   | 1   | 10.5 | 92 | 89.4 | 8.0 | 2.6 | 95.0 | 5.0 | 0 |
| 1 | 24  | 10.1 | 88 | 96.0 | 3.2 | .8  | 95.6 | 4.4 | 0 |
| 2 | 53  | 9.9  | 87 | 96.7 | 2.7 | .7  | 95.9 | 4.1 | 0 |
| 3 | 77  | 9.9  | 86 | 96.8 | 2.5 | .6  | 96.1 | 3.9 | 0 |
| 4 | 100 | 10.1 | 71 | 95.6 | 2.4 | 2.1 | 96.2 | 3.8 | 0 |
| 5 | 122 | 9.8  | 79 | 97.2 | 2.1 | .7  | 96.4 | 3.6 | 0 |
| 6 | 144 | 9.4  | 80 | 97.5 | 2.0 | .5  | 96.4 | 3.6 | 0 |
| 7 | 166 | 9.3  | 78 | 97.4 | 2.0 | .6  | 96.5 | 3.5 | 0 |
| 8 | 189 | 9.3  | 77 | 97.6 | 1.8 | .5  | 96.7 | 3.3 | 0 |
| 9 | 213 | 9.4  | 73 | 97.4 | 1.7 | .9  | 96.8 | 3.2 | 0 |

It will be evident from the above results that catalyst aging was very low, that selectivity to the desired ethyltoluene product was very high and that the para-ethyltoluene was the predominant isomer.

After 9 days of operation described above, the temperature was raised to 445° C., other conditions remaining the same and operation continued for 4 additional days. The results are summarized in Table VI below.

TABLE VI

| Day No. | Stream Time Hrs. | Mole % Conv. Toluene | Mole % Conv. C$_2$H$_4$ | Selectivity to Products, wt. % Ethyltoluene | Selectivity to Products, wt. % Other Aromatics | Selectivity to Products, wt. % Light Gas | Isomers in Ethyltoluene in Products, % Para | Isomers in Ethyltoluene in Products, % Meta | Isomers in Ethyltoluene in Products, % Ortho |
|---|---|---|---|---|---|---|---|---|---|
| 10 | 237 | 10.0 | 74 | 97.1 | 2.3 | .6 | 96.3 | 3.7 | 0 |
| 11 | 264 | 9.1  | 75 | 97.0 | 2.4 | .6 | 96.2 | 3.8 | 0 |
| 12 | 285 | 8.9  | 73 | 97.1 | 2.3 | .6 | 96.3 | 3.7 | 0 |
| 13 | 312 | 9.1  | 71 | 97.2 | 2.1 | .7 | 96.6 | 3.4 | 0 |

It will be seen from the above results that the aging rate was very slow and the overall catalyst performance was highly satisfactory.

EXAMPLE 7

HZSM-5 zeolite (60.5 grams) having a crystallite size of approximately 2 microns, containing 35 weight percent alumina binder, in the form of 1/16" extrudate, was steamed at 600° C. for 1 hour. It was thereafter impregnated with a solution of 38.7 grams of diammonium acid phosphate in 100 ml of water, dried and calcined at 500° C. overnight in an open dish. The resulting product was cooled and impregnated overnight with a solution of 195 grams of magnesium acetate tetrahydrate in 133 ml of water, dried and calcined at 500° C. for about 19 hours. The final catalyst contained 4.93 percent magnesium and 3.48 percent phosphorus by weight.

A sample of this catalyst was then treated with a mixture of toluene/hydrogen, WHSV 30/.08, mole ratio of 7.7/1, at 600° C., 100 psig for 10.8 hours.

EXAMPLE 8

Alkylation of ethylbenzene with ethylene to produce diethylbenzene was effected in the presence of the catalyst of Example 7. The ethylation reaction was carried out initially in the presence of hydrogen and thereafter in the presence of nitrogen, utilizing in each instance, equimolar amounts of ethylene and the diluent gas. Reaction conditions included a temperature of 425° C., a pressure of 100 psig, a feed mole ratio of ethylbenzene/ethylene/diluent gas of 6.1/1/3. With hydrogen, the ethylbenzene/ethylene/hydrogen feed WHSV was 30.2/1.2/0.24 and with nitrogen, the ethylbenzene/ethylene/nitrogen WHSV was 30.2/1.2/3.36.

The gaseous feed mixture was passed over the catalyst and the condensed liquid and gaseous products were analyzed by gas chromotography. Prior to operation, the catalyst was treated with hydrogen at 550° C., 100 psig for 5 hours (Run 1) and 3 hours (Run 2) respectively. The product results are summarized in Table VII below.

TABLE VII

| Time | % para-diethylbenzene |
|---|---|

| Run | Run Hours | Gas Diluent | Conversion, Mole % Ethylbenzene | Conversion, Mole % C$_2$H$_4$ | Total diethylbenzene |
|---|---|---|---|---|---|
| 1 | 42 | H$_2$ | 10.7–3.9[a] | 37–21 | 99.8–99.9 |
| 2 | 46 | N$_2$ | 11.6–2.6 | 31–6 | 99.8–99.7 |

| Run | p-diethyl-benzene | m-diethyl-benzene | o-diethyl-benzene | Light Gas | Benzene | Other Aromatics |
|---|---|---|---|---|---|---|
| 1 | 79.6–75.8 | .2–.1 | 0 | 1.0–.5 | 15.2–13.8 | 4.0–9.8 |
| 2 | 79. –80.2 | .1–.2 | 0 | 1.2–.5 | 14.8–10.9 | 4.2–8.2 |

[a]The ranges indicate the values for the first and last hour for the period indicated.

It will be evident from the above data that the rate of catalyst aging was greater with the nitrogen diluent than with the hydrogen diluent as shown by the ethylbenzene and ethylene conversion. Furthermore, the production rate of para + meta diethylbenzenes averaged 8.49 grams/hour with hydrogen diluent compared with 5.57 grams/hour with nitrogen, over a 50 percent increase. Exceptionally high selectivity to the para isomer in the diethylbenzene product was observed in both cases.

EXAMPLE 9

A sample of the catalyst described in Example 7 was calcined with air at 550° C. for 20 hours at atmospheric pressure and then used for the alkylation of ethylbenzene with ethylene in the presence of a hydrogen diluent and also in the presence of a nitrogen diluent, utilizing equal molar amounts ethylene and diluent gas. The reaction conditions used included a temperature of 425° C., a pressure of 100 psig, an ethylbenzene/ethylene/hydrogen feed WHSV of 29.7/1.2/0.24 or an ethylbenzene/ethylene/nitrogen feed WHSV of 29.7/1.2/3.47. The results are summarized in Table VIII below.

TABLE VIII

| Run | Time Run Hours | Gas Diluent | Ethylbenzene | C₂H₄ | % para-diethylbenzene Total diethylbenzene |
|---|---|---|---|---|---|
| 1 | 50 | H₂ | 21.9–16.3[a] | 65–55 | 98.4–98.9 |
| 2 | 50 | N₂ | 21.7–12.0 | 56–35 | 98.3–98.9 |

| Run | p-diethyl-benzene | m-diethyl-benzene | o-diethyl-benzene | Light Gas | Benzene | Other Aromatics |
|---|---|---|---|---|---|---|
| 1 | 70.4–79.1 | 1.2–.9 | 0 | 2.6– .7 | 20.5–16.6 | 5.4–2.7 |
| 2 | 70.9–82.1 | 1.2–.9 | 0 | 2.4–1.0 | 20.5–13.0 | 4.9–3.0 |

[a]The ranges indicate the values for the first and last hour for the period indicated.

It will be seen from the above results that the rate of catalyst aging was greater when the reactants were diluted with nitrogen as compared with hydrogen, under the same conditions, as shown by the conversion of starting materials. The total amount of diethylbenzene produced in the 50 hour period was 915 grams with the hydrogen diluent, compared with 810 grams with the nitrogen diluent. Thus, a clear advantage was observed when hydrogen was used as a diluent.

The following example will serve to illustrate the results obtained at atmospheric pressure.

EXAMPLE 10

The catalyst described in Example 1 was used to test the effect of cofeeding hydrogen with toluene and ethylene at atmospheric pressure. A toluene/ethylene feed WHSV of 6.9/0.5 was used. With hydrogen present, the toluene/ethylene/hydrogen feed WHSV was 6.9/0.5/0.036. A series of runs were made at 350 and 400° C. to compare the effect of adding one mole of hydrogen per mole of ethylene feed with runs in which hydrogen was absent. The results obtained are shown in Table IX below.

TABLE IX

| Run No. | Temp °C | Time Hours | Toluene Conv. % | Paraethyltoluene in total Ethyltoluene | Selectivity Ethyltoluene, % |
|---|---|---|---|---|---|
| WITHOUT HYDROGEN | | | | | |
| 1 | 350 | 0–1 | 13.8 | 97.8 | 89.8 |
| 2 | 350 | 1–2 | 12.3 | 97.8 | 92.5 |
| 3 | 350 | 2–18 | 9.6 | 98.1 | 95.3 |
| 4 | 350 | 18–19 | 7.4 | 98.3 | 95.2 |
| 5 | 350 | 19–20 | 7.1 | 98.3 | 95.9 |
| HYDROGEN ADDED | | | | | |
| 1 | 350 | 0–1 | 12.6 | 98.3 | 90.9 |
| 2 | 350 | 1–2 | 11.0 | 98.2 | 94.8 |
| 3 | 350 | 2–18 | 7.9 | 98.4 | 96.5 |
| 4 | 350 | 18–19 | 6.2 | 98.4 | 97.9 |
| 5 | 350 | 19–20 | 6.4 | 98.5 | 98.4 |
| WITHOUT HYDROGEN | | | | | |
| 1 | 400 | 0–1 | 18.5 | 95.7 | 92.6 |
| 2 | 400 | 1–2 | 18.8 | 95.9 | 94.7 |
| 3 | 400 | 2–19 | 16.3 | 96.3 | 97.5 |
| 4 | 400 | 19–20 | 14.8 | 96.8 | 97.7 |
| 5 | 400 | 20–21 | 14.8 | 96.8 | 98.1 |
| HYDROGEN ADDED | | | | | |
| 1 | 400 | 0–1 | 16.9 | 96.9 | 94.7 |
| 2 | 400 | 1–2 | 16.7 | 97.0 | 96.1 |
| 3 | 400 | 2–14 | 15.8 | 97.2 | 97.8 |
| 4 | 400 | 14–15 | 14.3 | 97.4 | 98.0 |

From the above results, it will be seen that although minor changes in toluene conversion were observed, selectivity to ethyltoluenes and production of the para isomer in ethyltoluene product were similar and there was no significant differences when hydrogen was added compared to similar runs in the absence of hydrogen. It is concluded from the above results that a hydrogen pressure in excess of atmospheric is essential in achieving the improvement in aging characteristics observed in accordance with the process of the invention.

What is claimed is:

1. Process for the ethylation of mono alkyl benzenes wherein the alkyl substituent contains 1 or 2 carbon atoms which comprises contacting the same with ethylene in the presence of hydrogen under conversion conditions including a temperature between about 350° and about 500° C., a pressure greater than atmospheric but less than 400 psig, employing a hydrogen to ethylene mole ratio in the approximate range of 0.5 1 to 10 and in the presence of a catalyst comprising a crystalline aluminoslicate zeolite, which zeolite is characterized by an activity in terms of alpha value, of between about 2 and about 5000, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said crystalline aluminosilicate zeolite further being characterized by a silica to alumina ratio of at least about 12 and a constraint index within the approximate range of 1 to 12, whereby aging of said catalyst during said ethylation is substantially reduced over comparable reaction carried out in the absence of hydrogen.

2. The process of claim 1 wherein said pressure is between about 50 and about 350 psig.

3. The process of claim 1 wherein said temperature is between about 400° and about 450° C. and said pressure is between about 100 and about 300 psig.

4. The process of claim 2 wherein the hydrogen to ethylene mole ratio is in the approximate range of 1 to 5.

5. The process of claim 1 wherein the ethylation of said mono alkyl benzene selectively produces the para and meta derivative thereof to the substantial exclusion of the ortho derivative.

6. The process of claim 1 wherein said mono alkyl benzene is toluene.

7. The process of claim 1 wherein said mono alkyl benzene is ethylbenzene.

8. The process of claim 1 wherein said crystalline aluminosilicate is ZSM-5.

9. The process of claim 1 wherein said crystalline aluminosilicate is admixed with a binder therefor.

10. The process of claim 8 wherein said ZSM-5 is admixed with a binder therefor.

11. The process of claim 1 wherein the crystalline aluminosilicate zeolite has undergone prior modification by combining therewith between about 0.5 and about 40 weight percent of at least one oxide selected from the group consisting of the oxides of phosphorus, antimony, boron and magnesium.

12. The process of claim 1 wherein the crystalline aluminosilicate zeolite has undergone prior modification by combining therewith between about 0.5 and about 25 weight percent of phosphorus.

13. The process of claim 1 wherein the crystalline aluminosilicate zeolite has undergone prior modification by combining therewith between about 1 and about 25 weight percent of an oxide of magnesium.

14. The process of claim 1 wherein the crystalline aluminosilicate zeolite has undergone prior modification by combining therewith between about 0.7 and about 15 weight percent of phosphorus and between about 1 and about 15 weight percent of an oxide of magnesium.

* * * * *

UNITED STATES PATENT AND TRADEMARK OFFICE
CERTIFICATE OF CORRECTION

PATENT NO. : 4,117,024
DATED : September 26, 1978
INVENTOR(S) : Warren W. Kaeding It is certified that error appears in the above—identified patent and that said Letters Patent are hereby corrected as shown below:

In Column 3, line 61, "in" before xylene should be -- of --.

In Column 14, Table 1 (last col.), "2.7-1.5" should be -- 7.7-1.5--.

Signed and Sealed this

Seventeenth Day of April 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,117,024

DATED : September 26, 1978

INVENTOR(S) : Warren W. KAEDING

It is certified that error appears in the above—identified patent and that said Letters Patent are hereby corrected as shown below:

Claim 1, line 12, change "0.51" to ---0.5---

Signed and Sealed this

Twenty-third Day of June 1981

[SEAL]

Attest:

RENE D. TEGTMEYER

*Attesting Officer*       *Acting Commissioner of Patents and Trademarks*